US008245706B2

(12) United States Patent
Namm

(10) Patent No.: US 8,245,706 B2
(45) Date of Patent: Aug. 21, 2012

(54) PRESSURE ACTIVATED REMOTE MICROPHONE

(75) Inventor: Joseph C. Namm, Plantation, FL (US)

(73) Assignee: Motorola Solutions, Inc., Schaumburg, IL (US)

( * ) Notice: Subject to any disclaimer, the term of this patent is extended or adjusted under 35 U.S.C. 154(b) by 412 days.

(21) Appl. No.: 12/488,945

(22) Filed: Jun. 22, 2009

(65) Prior Publication Data

US 2010/0322442 A1 Dec. 23, 2010

(51) Int. Cl.

| | |
|---|---|
| ***A62B 18/08*** | (2006.01) |
| ***A62B 18/02*** | (2006.01) |
| ***A61M 15/00*** | (2006.01) |
| ***F16K 31/02*** | (2006.01) |

(52) U.S. Cl. ......... 128/201.19; 128/200.24; 128/204.21; 128/205.25; 128/206.21

(58) Field of Classification Search .................. 381/122; 455/41.2; 128/201.19, 200.24, 200.26, 203.12–203.14, 128/204.18, 204.21, 204.23, 205.25, 206.21, 128/207.14, 207.18; 73/716; 2/173; 600/529, 600/532

See application file for complete search history.

(56) References Cited

U.S. PATENT DOCUMENTS

| | | | | |
|---|---|---|---|---|
| 4,827,964 | A | 5/1989 | Guido et al. | |
| 5,586,176 | A | 12/1996 | Peck | |
| 7,254,535 | B2 | 8/2007 | Kushner et al. | |
| 2006/0286933 | A1 | 12/2006 | Harkins et al. | |
| 2007/0283952 | A1 * | 12/2007 | Wilbur | 128/201.19 |

FOREIGN PATENT DOCUMENTS

| | | | |
|---|---|---|---|
| EP | 0288903 | B1 | 5/1993 |
| JP | 2008505538 | A | 2/2008 |
| KR | 20030073015 | A | 9/2003 |

OTHER PUBLICATIONS

International Search Report and Written Opinion for International Application No. PCT/US2010/036272 mailed on Jan. 4, 2011.
English language Abstract of KR Patent Publication No. KR20030073015, European Patent Office, espacenet database—Worldwide (2003).

* cited by examiner

*Primary Examiner* — Yuwen Pan
*Assistant Examiner* — George Monikang
(74) *Attorney, Agent, or Firm* — Barbara R. Doutre

(57) ABSTRACT

A pressure activated remote microphone is provided within a communication system (100). A face mask (102) incorporates a remote microphone (118) and one or more pressure sensor(s) (122). When a user puts on the mask (102), the remote microphone (118) is enabled in response to the pressure sensed by the pressure sensors (122). When the mask (102) is removed, the remote microphone (118) is disabled in response to the change in pressure sensed by the pressure sensor(s) (122).

18 Claims, 4 Drawing Sheets

PRESSURE ACTIVATED REMOTE MICROPHONE

FIELD OF THE DISCLOSURE

The present disclosure relates generally to communication devices and more particularly to a remote microphone used in conjunction with a face mask.

BACKGROUND

Two-way radios, cell phones, and other handheld communication devices are often used in environmentally hazardous areas. Good, reliable communications among personnel engaged in hazardous environmental activities, such as fire fighting, are essential for accomplishing their missions while maintaining their own health and safety. Working conditions may require the use of a pressurized air delivery system, such as a Self Contained Breathing Apparatus (SCBA) mask and air delivery system. A remote microphone is sometimes included within the mask to communicate with a portable radio used by the firefighter to communicate with others. The remote microphone used within the safety mask is battery operated and thus must be manually turned on and off by the user. Also, when the mask is removed, the remote microphone may still be activated making it awkward for the user to transmit.

Accordingly, there is a need to facilitate the use of a remote microphone in a safety mask.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method, steps and apparatus components related to a communication system utilizing a pressure activated remote microphone incorporated within a face mask. The face mask may cover the user's entire face and/or cover the user's nose and mouth.

In the description herein, numerous specific examples are given to provide a thorough understanding of various embodiments of the invention. The examples are included for illustrative purpose only and are not intended to be exhaustive or to limit the invention in any way. It should be noted that various equivalent modifications are possible within the spirit and scope of the present invention. One skilled in the relevant art will recognize, however, that an embodiment of the invention can be practiced with or without the apparatuses, systems, assemblies, methods, components mentioned in the description.

Figure 1:
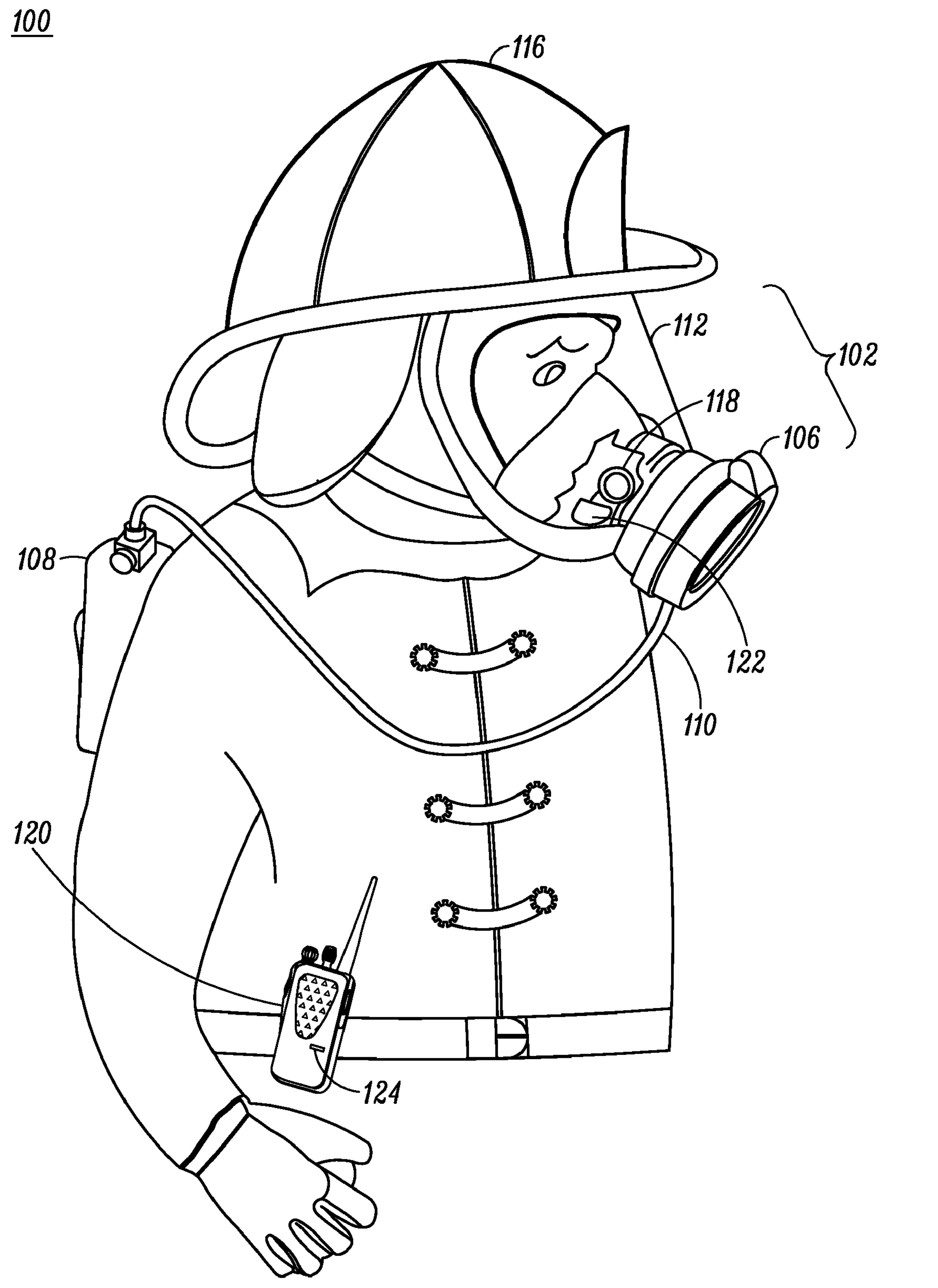
FIG. 1 is a communication system in accordance with various embodiments of the invention.

FIG. 1 is a communication system in accordance with various embodiments of the invention. Communication system 100 comprises a breathing mask 102, such as a self contained breathing apparatus (SCBA), worn by a user 104, such as a firefighters Mask 102 comprises a regulator portion 106 coupled to a pressurized air supply cylinder 108 via a pressurized air supply channel 110. The mask 102 provides an enclosed air cavity forming a gas impermeable seal about the user's nose and mouth. The mask may further include a face shield 112 designed to provide an airtight, gas impermeable seal around the user's entire face. A heat shield 114 and helmet 116 may also be worn by the user 104. In accordance with the various embodiments of the invention, mask 102 includes a microphone, referred to as remote microphone 118 and at least one pressure sensor 122 coupled to the mask for controlling the remote microphone. Remote microphone 118 communicates with radio 120 which may be a portable two-way radio or similar communication device utilized by user 104. Remote microphone 118 may also be a remote speaker microphone, but for the purposes of this application, the microphone aspect is being described.

The remote microphone 118 communicates wirelessly with the portable radio 120 using a personal area network (PAN) such as Bluetooth or other short range communication system. Pressure sensor 122 is used to enable and disable the remote microphone 118 in response to a predetermined pressure change in the mask. For example, a SCBA mask uses positive pressure to assure that contaminants do not enter the mask via a faulty seal while in use. When the user 104 is wearing the mask 102 and air is flowing to the user, the air inside the mask is pressurized to approximately 1.5 inches of water above the ambient atmosphere. By using the increase in pressure to turn on the remote microphone 118, the user 104 does not have to manually turn the remote microphone on. When the mask 102 is removed, the mask pressure drops. By using the drop in pressure to turn off the remote microphone 118, the user does not have to manually turn the remote microphone off. Additionally, the microphone audio can be routed based on the pressure.

The remote microphone audio can be routed based on pressure in the mask 102. For example, while the mask is worn by the user 104, and the user is breathing pressurized air in the mask, the user can speak into the mask's microphone and that audio is routed to the portable radio for transmission to other communication devices. Upon removal of the mask 102, the remote microphone 118 is disabled after a predetermined time delay in which a pressure difference between the inside of the mask and the outside of the mask is no longer present. When the mask 102 is not worn, the user can speak into the portable radio's microphone 124 without making any manual adjustments to the remote microphone 118.

Various embodiments are supported by having one or more pressure sensors 122 incorporated within the mask 102. One pressure sensor may be used to monitor pressure sensed inside the mask 102 or two or more sensors may be used to monitor differential pressure between the inside and the outside of the mask 102. The remote microphone 118 is automatically powered on with the increase in mask pressure over ambient air pressure. The remote microphone audio is transmitted to the portable radio 120 while the mask pressure is above the local ambient pressure. The remote microphone is automatically powered off when the mask pressure is equivalent to the ambient air pressure. An optionally configurable delay can be implemented to ensure that mask use has ended. The delay is established from the time the mask 102 reaches ambient pressure and is used to avoid intermittent switching of the device when the user takes deep breaths or when the air cylinder is being changed but is still operating within an immediate danger to life or health (IDLH) environment.

Figure 2:
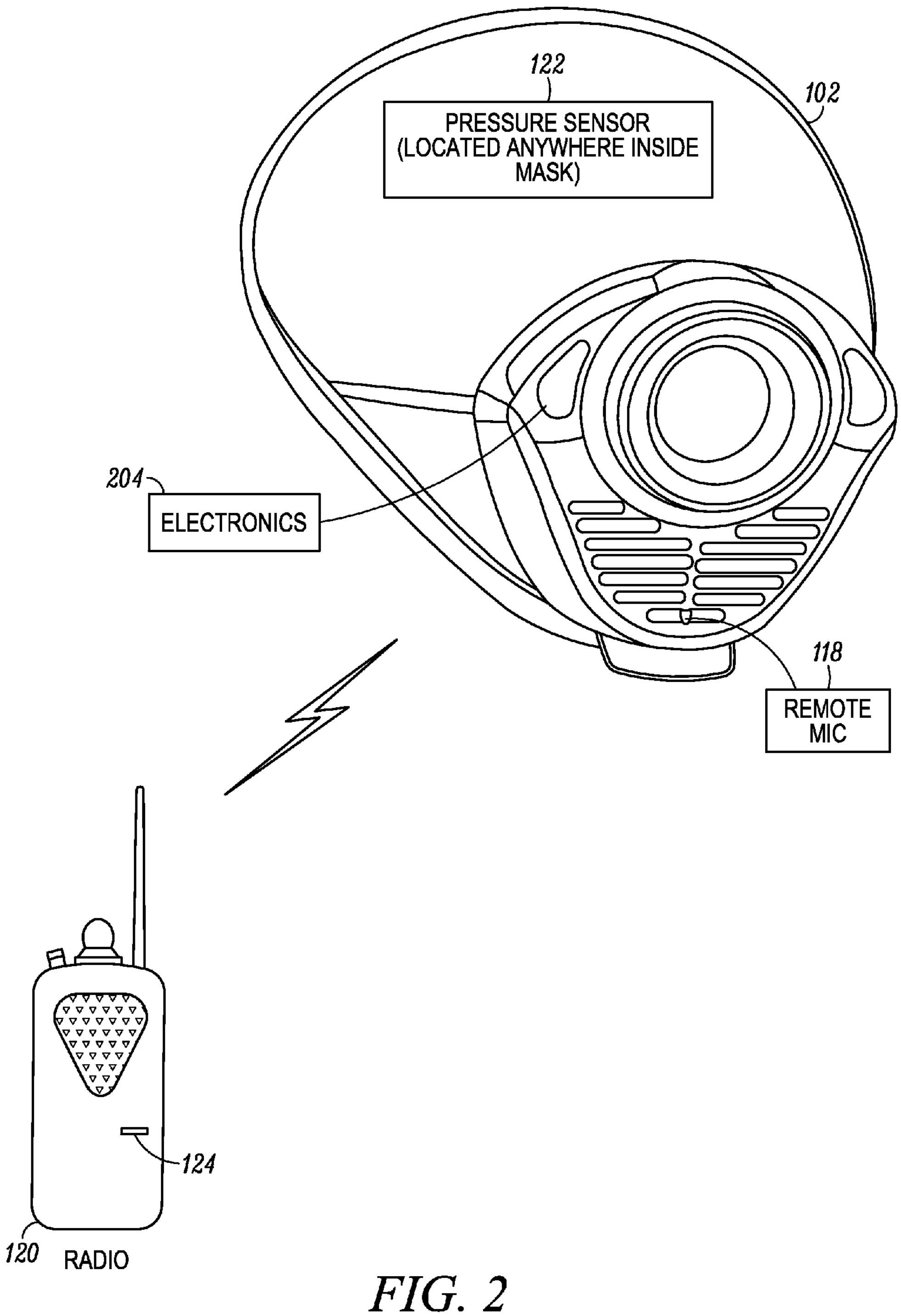
FIG. 2 is a partial block diagram of the communication system of FIG. 1 in accordance with various embodiments of the invention.

FIG. 2 is a partial block diagram of the communication system of FIG. 1 in accordance with various embodiments of the invention. The communication system comprises a pressure activated communication device formed of the mask 102, the remote microphone 118 coupled to the mask, and one or more pressure sensor(s) 122 coupled to the mask for controlling the remote microphone. The pressure sensors 122 may be located anywhere inside the mask 102 and for differential pressure sensing there may be a pressure sensor located on the outside of the mask as well. The regulator portion 106 forms an enclosed air cavity within which interface electronics 204 are situated for coupling the pressure sensors 122 to the remote microphone 118. The remote microphone 118 is enabled and disabled in response to pressure sensed by the pressure sensors 122, and microphone audio is routed based on pressure sensed by the pressure sensor. When the mask is removed from the user's face, the remote microphone 118 is disabled and the portable radio microphone 124 is enabled in response to the mask pressure being at ambient pressure for a predetermined amount of time.

In the embodiment of FIG. 2, the remote microphone 118, pressure sensors 122 and interface electronics 204 fit within the air cavity portion of the mask 102, however other locations within the mask may also be used depending on the mask configuration. For face masks having a face shield, the entire area covering the face is pressurized and thus a plurality of pressure sensors can be used to sense differential pressure inside and outside of the mask 102 if desired. For optimal audio performance, the remote microphone 118 is preferably located in front of the user's mouth. However the remote microphone may be located anywhere inside the mask 102 as suits the configuration.

Figure 3:
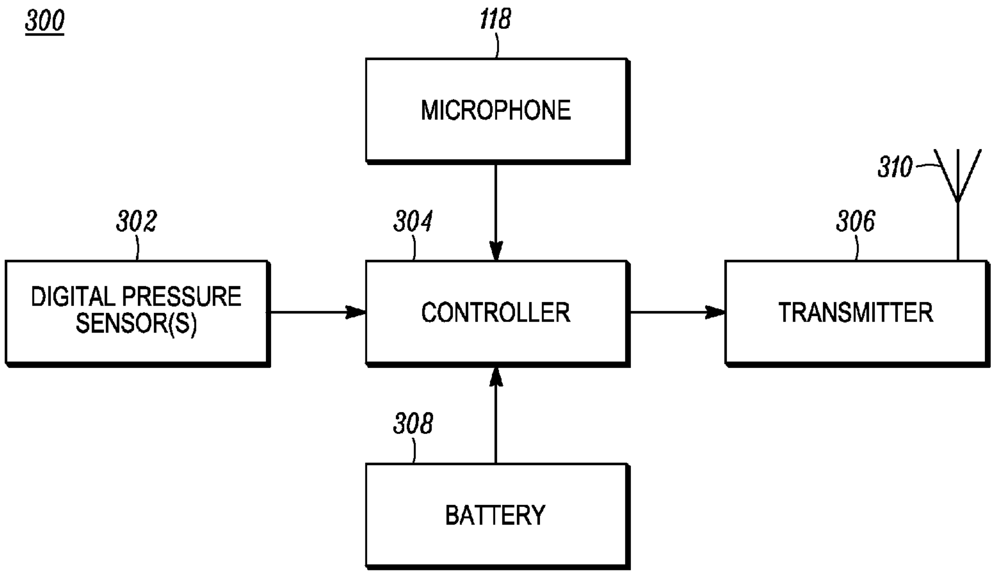
FIG. 3 is a block diagram of a pressure activated communication device incorporated within the mask of FIG. 1.
Figure 4:
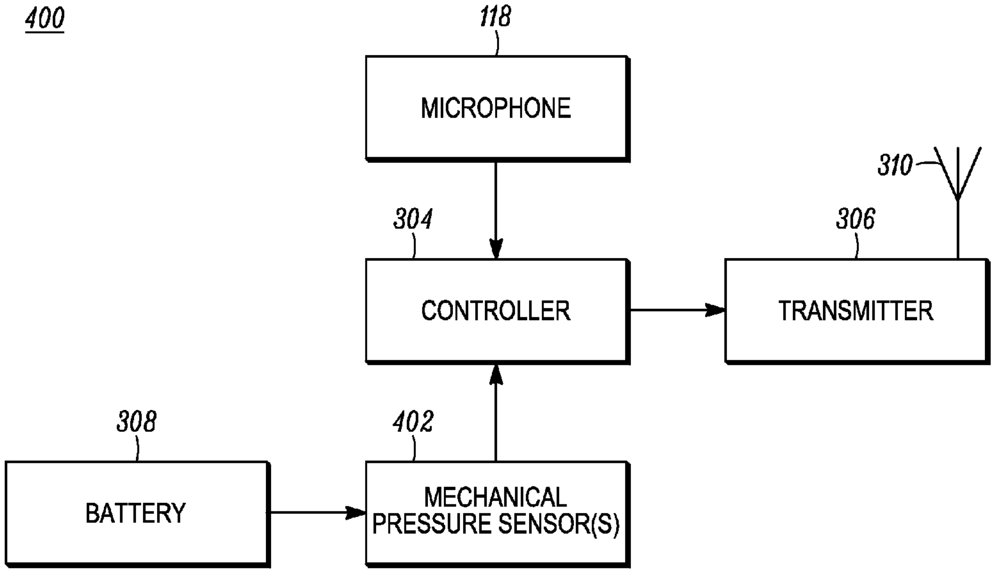
FIG. 4 is another block diagram of a pressure activated communication device incorporated within the mask of FIG. 1

FIG. 3 is a block diagram of the interface electronics for the remote microphone 118 of FIGS. 1 and 2 which provide for a pressure activated communication device 300. Pressure activated communication device 300 includes the remote microphone 118, digital pressure sensor(s) 302, controller 304, transmitter 306, battery 308, and antenna 310. In operation the controller 304 receives sensed pressure readings from the digital pressure sensor(s) 302, the controller enabling and disabling the remote microphone 118 in response to changes in the sensed pressure. FIG. 4 is another block diagram of interface electronics for the remote microphone 118 of FIGS. 1 and 2 which provide for a pressure activated communication device 400. Pressure activated communication device 400 includes remote microphone 118, mechanical pressure sensor(s) 402, controller 304, transmitter 306, battery 308, and antenna 310. In operation the controller 304 receives sensed pressure changes from the mechanical pressure sensors 402. The controller 304 enables and disables the remote microphone 118 in response to changes in the sensed pressure. The block diagram of FIGS. 3 and 4 are provided to show that digital pressure sensors and/or mechanical pressure sensors may be used without departing from the scope of the invention.

Figure 5:
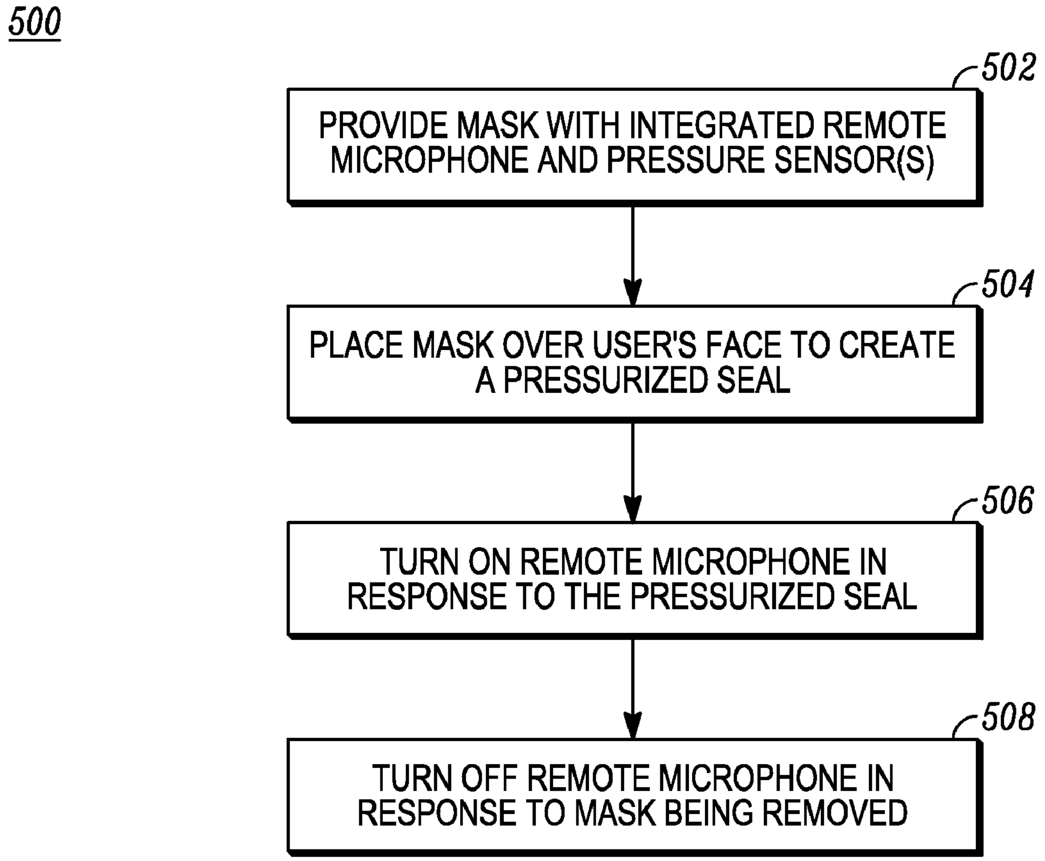
FIG. 5 is a flow chart of a method utilizing the communication system of FIG. 1 in accordance with various embodiments of the invention.

FIG. 5 is a flow chart of a method utilizing the communication system of FIG. 1 in accordance with various embodiments of the invention. The method begins at 502 by providing a mask to a user, the mask having a remote microphone and pressure sensor integrated therein. By placing the mask to the user's face to form a pressurized seal at 504, the remote microphone is automatically turned on in response to the sensed pressurized seal at 506. The remote microphone is turned off at 508 in response to the mask being removed from the user's face. As previously described, the remote microphone is enabled or turned on by sensing an increase in pressure, and the remote microphone is disabled or turned off in response to the mask being removed due to the equalization of pressure between the mask ambient pressure. As previously mentioned, a delay may be configured to ensure that the mask 102 has been removed. Once the mask is removed, communication reverts to the portable radio via the portable radio's microphone.

Accordingly, there has been provided a pressure activated remote microphone for use within a communication device and system. By incorporating pressure sensor(s) and a remote microphone within a mask, mask pressure sensed by the sensor(s) is used to control the microphone and route audio. The user is provided with the advantage of no longer having to manually turn the microphone on and off to enable and disable the remote microphone. Automatically enabling the remote microphone when the mask is worn, and automatically disabling the remote microphone when the mask is taken off saves battery power. By reverting the audio functionality automatically back to the portable radio when the mask's remote microphone is disabled, the user is able to remove the mask and immediately begin using the radio without having to make any adjustments to the radio. The improved interface provided by the pressure activated remote microphone allows the user to speak into the remote microphone of the mask while the mask is worn and speak into the radio microphone when the mask is not worn. In hazardous environments where the user is often wearing gloves the improved interface provided by the pressure activated remote microphone is particularly beneficial.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject Those skilled in the art will appreciate that the above recognized advantages and other advantages described herein are merely exemplary and are not meant to be a complete rendering of all of the advantages of the various embodiments of the present invention.

I claim:

1. A communication device, comprising:

a mask;

a remote microphone coupled to the mask; and a pressure sensor coupled to the mask for controlling the remote microphone, wherein the remote microphone of the mask is disabled in response to the mask pressure being at ambient air pressure for a predetermined amount of time.

2. The communication device of claim 1, wherein microphone audio is routed based on pressure sensed by the pressure sensor.

3. The communication device of claim 1, wherein the mask comprises a breathing mask.

4. The communication device of claim 3, wherein the breathing mask comprises a self contained breathing apparatus face mask.

5. A communication system, comprising:

a radio;

a mask;

a remote microphone coupled to the mask, the remote microphone communicating with the radio; and at least one pressure sensor coupled to the mask for controlling the remote microphone, wherein the remote microphone of the mask is disabled and a microphone at the radio is enabled in response to the mask pressure being at ambient air pressure for a predetermined amount of time.

6. The communication system of claim 5, wherein the radio comprises a portable radio.

7. The communication system of claim 6, wherein the remote microphone comprises a battery powered remote microphone and the remote microphone communicates wirelessly with the portable radio.

8. The communication system of claim 5, wherein the remote microphone audio is routed based on pressure in the mask.

9. The communication system of claim 5, wherein the at least one pressure sensor enables and disables the remote microphone in response to a predetermined pressure change in the mask.

10. The communication system of claim 5, wherein the remote microphone is disabled after a predetermined time delay in which a pressure difference between the inside of the mask and the outside of the mask is no longer present.

11. The communication system of claim 5, further comprising:

a controller for receiving pressure change inputs from the at least one pressure sensor, the controller enabling and disabling the remote microphone; and a battery for supplying power to the controller, the at least one pressure sensor, and the remote microphone.

12. The communication system of claim 11, wherein the at least one pressure sensor comprises a mechanical pressure sensor.

13. The communication system of claim 11, wherein the at least one pressure sensor comprises a digital pressure sensor.

14. The communication system of claim 11, wherein the at least one pressure sensor comprises a plurality of sensors sensing differential pressure.

15. The communication system of claim 5, wherein the remote microphone is automatically powered on with an increase in mask pressure over ambient air pressure and the remote microphone is automatically powered off when the mask pressure is equivalent to the ambient air pressure.

16. The communication system of claim 15, wherein the remote microphone is automatically powered off when the mask pressure is at ambient air pressure for a predetermined amount of time.

17. The communication system of claim 16, wherein the remote microphone audio is transmitted to the radio while the mask pressure is above the ambient air pressure.

18. A communication system, comprising:

a radio comprising a microphone;

a mask for placing on a user's face to form a pressurized seal;

a remote microphone coupled to the mask, the remote microphone communicating with the radio; and at least one pressure sensor coupled to the mask for sensing the pressurized seal, wherein in response to the sensed pressurized seal, the remote microphone is turned on, and in response to the mask being removed from the user's face, the remote microphone is turned off and the microphone at the radio is turned on.

* * * * *

UNITED STATES PATENT AND TRADEMARK OFFICE

CERTIFICATE OF CORRECTION

PATENT NO. : 8,245,706 B2
APPLICATION NO. : 12/488945
DATED : August 21, 2012
INVENTOR(S) : Namm It is certified that error appears in the above-identified patent and that said Letters Patent is hereby corrected as shown below:

In Column 2, Line 19, delete “firefighters Mask 102” and insert -- firefighter. Mask 102 --, therefor.

Signed and Sealed this
Nineteenth Day of February, 2013

Teresa Stanek Rea
*Acting Director of the United States Patent and Trademark Office*